United States Patent [19]

Goodrum

[11] Patent Number: 4,622,036
[45] Date of Patent: Nov. 11, 1986

[54] POROUS FILM AND ABSORPTIVE STRUCTURE

[75] Inventor: Richard W. Goodrum, Richmond, Va.

[73] Assignee: Ethyl Corporation, Richmond, Va.

[21] Appl. No.: 627,027

[22] Filed: Jul. 2, 1984

Related U.S. Application Data

[63] Continuation-in-part of Ser. No. 365,424, Apr. 5, 1982, abandoned.

[51] Int. Cl.$^4$ ............................................. A61F 13/16
[52] U.S. Cl. ................................... 604/367; 604/369; 604/370; 604/372; 604/378; 604/379; 604/380; 604/381; 604/382; 428/314.2; 428/315.7; 428/315.9
[58] Field of Search ............... 604/367, 369, 370, 372, 604/381, 382, 378, 379, 380; 428/314.2, 315.7, 315.9

[56] References Cited

U.S. PATENT DOCUMENTS

| | | | |
|---|---|---|---|
| 3,929,135 | 12/1975 | Thompson | 128/287 |
| 4,000,028 | 12/1976 | Hoey | 156/79 |
| 4,054,141 | 10/1977 | Schwaiger et al. | 128/287 |
| 4,145,464 | 3/1979 | McConnell et al. | 428/171 |

Primary Examiner—John Kight
Assistant Examiner—M. L. Moore
Attorney, Agent, or Firm—Donald L. Johnson; John F. Sieberth; Paul H. Leonard

[57] ABSTRACT

An absorptive structure for absorbing and containing fluids from a source exterior of said structure comprising a topsheet, an absorbent element and a back sheet, wherein said topsheet is a liquid permeable material formed from particles of non-dissolvable polymeric materials partially fused together to form a continuous sheet and has a multiplicity of openings therein of a predetermined size and shape so as to direct fluid flow into the absorbent element and inhibit fluid flow from the absorbent element through the topsheet, and said back sheet is impervious to liquids.

17 Claims, 3 Drawing Figures

POROUS FILM AND ABSORPTIVE STRUCTURE

CROSS-REFERENCE TO RELATED APPLICATION

This application is a continuation-in-part of application Ser. No. 365,424, filed Apr. 5, 1982, now abandoned.

BACKGROUND OF THE INVENTION

1. Field of the Invention

The present invention is in the field of plastic films or sheets and more particularly relates to porous or liquid permeable thermoplastic films.

Porous or perforated thermoplastic films have many useful applications. Such films are useful in gardening and farming to prevent the growth of grass or weeds while permitting moisture to be transmitted through the film to the solid beneath. They are used for making disposable diapers and other various absorbent structures and for packaging of foods and other materials.

The invention also relates to absorptive structures made from the porous film, such as diapers, sanitary napkins, bed pads, incontinent pads, towels, bandages and the like. The invention particularly relates to porous film used as topsheets for such structures.

The invention especially relates to an improved porous film or topsheet which allows fluid to pass to the interior of the absorptive device but which inhibits the reverse flow of the fluid. In general, the topsheet is the portion of an absorptive device which covers one face of the absorbent element of the absorptive structure and which in some applications contacts the skin of a person using the absorptive device.

2. Description of the Prior Art

Particularly useful absorptive devices are articles of manufacture designed to receive and retain fluid discharges from the body within an absorbent element of the absorptive device. Absorptive devices such as sanitary napkins, catamenial tampons, bed pads, incontinent pads, towels, bandages and the like are well known articles of commerce. In recent times, single use disposable absorptive devices have significantly replaced permanent absorptive devices which were designed to be laundered and reused. While the improved absorptive structure of this invention can be used with reusable absorptive devices, it finds great utility when used with disposable absorptive devices.

Perforated thermoplastic films of polyethylene, polypropylene, polybutene-1, polyvinyl chloride, and other flexible thermoplastics normally extruded into such films or thin sheets have been made by various methods. One method is to extrude the thermoplastic material, e.g., polyethylene, from a conventional slot extrusion die onto a continuously moving, smooth, cooled casting surface, e.g., a chill roll. A pattern may be applied to the chill roll and the film pressed to the roll while in the amorphous or molten stage by press rolls. Alternatively, the chill roll may be very smooth and a desired pattern in the film may be mechanically impressed into the film on the chill roll by pressing the roll against the film and the chill roll to impress the pattern into the film as it is cooled on the chill roll. The softness of the film produced by chill casting is directly related to the density of the polyethylene resin used. In order to obtain different degrees of softness or stiffness, it is necessary to use a number of polyethylene resins having different densities. Thus, if it is desired to produce a relatively stiff embossed film, it is necessary to use more expensive polymers having high densities as the feed material to the slot die.

Film rolls of poor conformation produce problems when running the film through fabricating machines or through a film printing apparatus.

An example of a method and apparatus for producing film according to the foregoing slot die-chill cast roll technique is shown in U.S. Pat. No. 3,374,303.

Another technique used for making plastic film has been the utilization of a heated engraved embossing roll in conjunction with a backup roll. The preformed strip of thermoplastic film normally at room temperature, is passed between the nip of a heated engraved roll and a backup roll and is embossed by being heated while in contact with the heated, engraved roller. The resultant embossed film usually has a very shallow and poorly defined pattern. An example of an apparatus and process for carrying out a process of this type is shown in U.S. Pat. No. 3,176,058.

Still another process for making thermoplastic film has been to pass the film over a heated roll or a series of heated rollers in order to heat the film to a softened state and then to contact the film with an embossing roller and to press the film against the embossing roller by a backup roller. Normally, the embossing roller and the backup rollers are cooled in order to freeze the pattern into the film so that it may be immediately wound up into rolls, if desired. An apparatus and process for preparing an embossed film according to the foregoing is shown in U.S. Pat. No. 3,246,365.

A more recent process for making plastic material is shown in U.S. Pat. No. 3,950,480, wherein the film is heated by a non-direct contact heat source to raise the temperature of the film above its softening point and the film is then immediately fed between adjacent, counter-rotating rollers, and thereby embossed.

A method for perforating thermoplastic sheet or film is disclosed in U.S. Pat. No. 3,054,148, issued to Zimmerli, which reference is hereby incorporated herein. The Zimmerli patent discloses a stationary drum having a molding element mounted around the outer surface of the drum which is adapted to rotate freely thereon. A vacuum chamber is employed beneath the screen or molding element to create a pressure differential between the respective surfaces of the thermoplastic sheet to cause the plasticized sheet to flow into the perforations provided in the molding element and thereby cause a series of holes to be formed in the sheet.

U.S. Pat. No. 4,155,693 and U.S. Pat. No. 4,157,237 illustrate types of screens or molding elements.

U.S. Pat. No. 4,252,516 and U.S. Pat. No. 4,317,792 disclose apparatus and method, respectively, for manufacturing thermoplastic sheet having elliptical holes.

Disposable absorptive devices comprising an absorbent pad covered with a topsheet which contacts the body are well known. Covering the outer portion of the absorptive device with a fluid-impermeable backsheet to prevent absorbed fluids from leaking out of the absorptive device and soiling clothing, bed clothes, etc. is equally well known. The absorbent pad component of disposable absorptive devices can comprise well known materials such as creped cellulose wadding, airlaid felt or the like. The liquid impermeable backsheet can comprise any of various materials well known in the art such as polyethylene film.

One of the principle disadvantages of conventional absorptive devices is the maceration of the skin caused by prolonged contact with absorbed fluids. One especially common manifestation of this maceration is diaper rash generally occurring about the base of the trunk of infants. In order to minimize the effect of prolonged liquid contact with the skin, absorptive devices such as diapers have been produced with the body contacting topsheet thereof designed to exhibit a greater or lesser degree of surface dryness. For example, U.S. Pat. No. 3,327,625 issued to Johnson on Mar. 1, 1966, teaches that any hydrophobic material in the crotch area of the diaper will cause moisture to wick away from the skin of an infant wearer and thereby provide a substantially dry surface in contact with the infant's skin. U.S. Pat. No. Re. 26,151 issued to Duncan et al. on Jan. 31, 1967 teaches the use of porous, hydrophobic, nonwoven fabrics as topsheets. U.S. Pat. No. 2,916,037 issued to Hansen on Dec. 8, 1959, is a further example of the use of a nonwoven topsheet.

U.S. Pat. No. 3,814,101 issued to Kozak on June 4, 1974 illustrates still another type of disposable absorbent article. Such patent discloses a topsheet of non-fibrous hydrophobic film which has a plurality of valvular openings or slits therein and a system of depressed areas disposed across the surface of the topsheet. The openings permit the flow of liquid in one direction of the absorbent but reduce the flow of the liquid in the opposite direction.

U.S. Pat. No. 3,989,867 which issued to Sisson on Nov. 2, 1976, describes a breathable liquid impervious backsheet containing apertured bosses. The apertures therein, in order to maintain the liquid impervious character of the backsheet, are smaller in diameter than the capillaries of U.S. Pat. No. 3,929,135 hereinafter described.

U.S. Pat. No. 3,929,135 issued to Thompson on Dec. 30, 1975, relates to absorptive devices utilized a topsheet having tapered capillaries of critical diameters and tapers which allow fluid to pass into the interior of an absorptive device and which inhibit the reverse flow of such fluid.

SUMMARY OF THE INVENTION

The present invention relates to a unique porous sheet of thermoplastic material, a perforated porous sheet or film and an absorptive device made from such sheets or film. The porous film comprises a liquid permeable material formed from particles of non-dissolvable polymeric materials partially fused together to form a continuous sheet. The sheet may also have a multiplicity of additional openings or perforations therein of a predetermined size and shape so as to direct the flow of fluids in one direction or into an absorbent element and to inhibit the flow of fluids in the other direction or from the absorbent element through the sheet. The backsheet is substantially impervious to liquids. The perforations or additional holes may be added to the sheet by slitting, perforating, or any other suitable means.

The sheet of the instant invention is an improvement over prior art sheets in that it enhances the free transfer of fluids into an absorbent substrate and more effectively inhibits the reverse flow of the fluids from the substrate. The sheet or film closely resembles and feels like very soft cloth.

It is therefore a principal object of the present invention to provide a porous plastic film constructed of partially heat fused fine polymeric particles.

It is another object of the invention to provide a porous plastic film which has an additional multiplicity of small perforations or openings therein.

Still another object of the present invention to provide an absorptive structure for absorptive devices which enhances the free transfer of fluids from an exterior source into a substrate absorbent element while effectively inhibiting the reverse flow of fluids from the absorbent element.

An important object of the present invention is to provide a sheet or topsheet for absorptive devices or other use which feels smooth to the human touch and has the feeling of cloth.

BRIEF DESCRIPTION OF THE DRAWINGS

The construction designed to carry out the invention will be hereinafter described, together with the features thereof.

The invention will be more readily understood from a reading of the following specification and by reference to the accompanying drawings forming a part thereof, wherein an example of the invention is shown and wherein.

DESCRIPTION OF THE PREFERRED EMBODIMENTS

Figure 1:
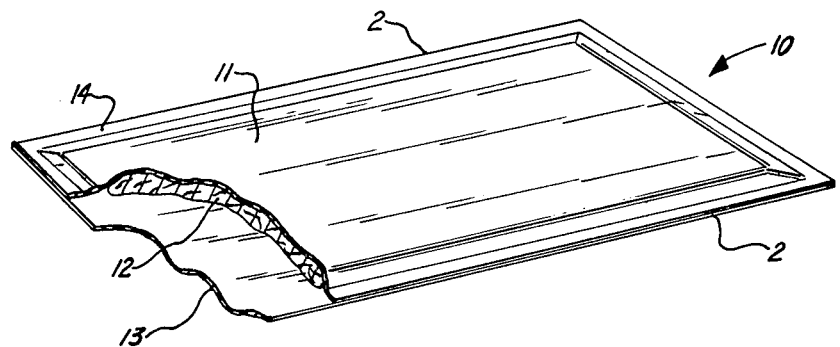
FIG. 1 is a perspective representation of an absorptive structure of the invention with a portion of its components cut away.
Figure 2:
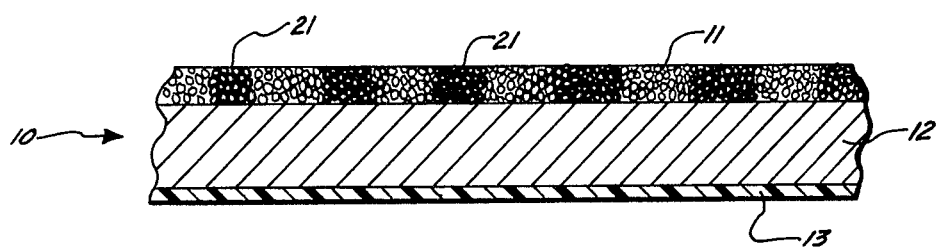
FIG. 2 is an enlarged cross-section in elevation of the absorptive structure taken along line 2—2 of FIG. 1.

The absorptive structure of the invention is generally referred to by the reference numeral 10. The novel porous film or topsheet of this invention is shown at 11. The other major components of the absorptive structure 10 are the absorbent element or pad 12 and the backsheet sheet 13. In the drawings, like characters of references designate like parts throughout the several views.

In general, the side flaps 14 of the backsheet 13 are folded so as to cover the edges of the absorbent pad 12 and topsheet 11. Such arrangement completely seals in the absorbent pad 12. Any other arrangement for sealing the edges of the absorbent structure may be used without departing from the scope of the invention.

The structure of the porous film or topsheet 11 comprises a plurality of particles 20 of non-dissolvable materials partially fused together at 21 to form a continuous sheet. The continuity of the particles is further interrupted by a multiplicity of openings 22 which may be in the shape of slits, dimples, funnels, tapered capillaries, cylinders or other geometric and asymmetric shapes and may be varied in size and frequency to suit the particular viscosity; density, mass and flow rates of the fluid to be absorbed. U.S. Pat. No. 3,929,135 and U.S. Pat. No. 3,814,101 illustrate openings or holes of a suitable size and shape, and such references are specifically incorporated herein.

Figure 3:
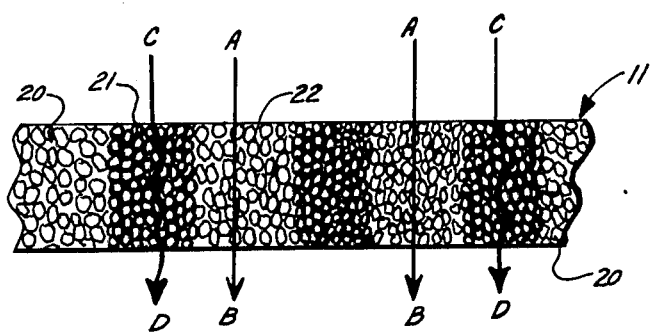
FIG. 3 is an enlarged cross-section of a porous sheet or film of the invention and the topsheet of FIG. 2.

It can readily be seen in FIG. 3, that fluids flow directly through the porous film or topsheet from A to B and also may flow indirectly from C to D.

Aesthetically, the structure of the porous film or topsheet closely resembles and feels like very soft cloth. Ideal particle sizes are those which are small enough to feel smooth to a human touch. Particles from about 0.003 inches to about 0.004 inches in diameter are suitable. Sizes as small as 1 or 2 microns and as large as 2000 microns are also suitable.

It is not necessary, of course, that the particles all be of the same size. A mixture of particles of various sizes within the desired range of sizes is quite suitable. In fact, such particles are normally obtained as mixtures of various sizes of particles. Materials which have been found to meet the specifications and which are generally supplied in particle form are polymeric materials such as the new so-called linear low density polyethylenes, high density polyethylenes, polypropylene and polyvinylchloride (PVC).

Fusing sintered particles of all sorts of materials that melt with heat and pressure are well known and old in the art. The porous film of the invention is made by the application of such art in a continuous process. Although the particles are relatively small, heat and pressure are applied thereto only in an amount sufficient to provide a desired fusion which in turn provides a desired degree of porosity. The particles themselves are not permeable. It is only the spaces provided from partially fusing the particles which provides permeability to the sheet. Perforating the finished sheet provides additional permeability, if such is desired.

Additional strength may be imparted to the porous film or sheet by post orienting in one or two directions by the use of a tentering frame which also increases the rate of fluid flow through the sheet.

The manufacture of the porous sheet may be by any suitable method such as dispersion of the polymeric particles on a moving belt followed by heating to a temperature appropriate for the desired degree of fusion of the polymeric particles thereby forming the porous sheet. Then passing the sheet through a set of pressure rollers, cooling and then stripping the sheet from the belt and winding the sheet into a roll. A variation of such process provides for preheated particles being distributed into the nip of an embossing set of rollers wherein the particles under pressure from the embossed rolls are fused and simultaneously embossed with a pattern of holes designed to increase the porosity of the sheet. Selection of the particular embossed pattern along with variations in particle size may be combined over a wide range of shapes, frequency and sizes to impart not only increased flowability through the topsheet but improved functionality and aesthetically pleasing and comfortable surfaces. Post orientation may further enhance such properties while improving the strength characteristics of the sheet.

Excluding the area of holes formed by the vacancies between partially fused particles, a porous sheet with total projected open area resulting from the geometrically or asymmetrically shaped holes added to the sheet by embossing, perforating, piercing, vacuum forming or other processes used to impart holes and prior to post orienting of from less than about 1% to about 64% of the total area, satisfies the requirements of the practical uses of the invention and also satisfies the requirements of servicability for strength applications. Beginning with such percentages of open areas, post orienting can double the stated projected areas on the minimum side up to increasing the projected area to about 50 times on the maximum side. The maximum would represent a seven-fold stretch of the base sheet in both transverse and machine direction. Such amount has been found to enhance the desired properties from the olefin polymers found to be most suitable in such applications.

A projected open area in the porous sheet of about 5% represents holes, whether geometric in design or asymmetric. The holes or openings have a mean diameter of 0.005 inches spaced and average of 0.020 inches apart. A projected area of about 20% may be obtained by holes with a mean diameter of either 0.005 inches, 0.010 inches, 0.020 inches, 0.50 inches, or 0.10 and with respective spacing of 0.010 inches, 0.20 inches, 0.040 inches, 0.10 inches and 0.20 inches. A practical maximum projected hole area for a non-oriented, porous sheet is about 70% due to the fragility of the connecting pieces between holes. Projected area percentages are based on square inch sized areas.

The topsheet of the invention is constructed of finely divided particles which range from a size of about 0.003 inches to a size of about 0.004 inches or from about 1 to about 2000 microns. These finely divided particles are partially fused together by heat to provide a thin porous sheet having a thickness of from about 0.0005 inches to about 0.25 inches.

If the porous sheets hereindescribed are post oriented through a tentering apparatus to high degree, projected areas must be based on units larger than square inches, e.g., square feet.

The thickness of the non-oriented porous sheet varies from about 0.0005 inches to about 0.250 inches depending upon the particle size and the particular embossing pattern. Orientation also reduces these thicknesses in direct proportion to the degree of orientation.

The foregoing disclosure and description of the invention is illustrative and explanatory thereof and various changes in the illustrated structure may be made within the scope of the appended claims without departing from the spirit of the invention.

What is claimed is:

1. A liquid permeable sheet material having the feel and resemblance of soft cloth consisting essentially of particles of non-dissolvable polyolefin or polyvinylchloride polymeric materials partially fused together by heat so as to provide a desired amount of liquid permeability through the spaces provided by the partial fusion of said particles, said particles ranging in size, from about one micron to about 2000 microns, and said sheet having a thickness of about 0.0005 inches to about 0.25 inches.

2. The sheet of claim 1, wherein said particles of non-dissolvable polymeric materials are post oriented to improve strength of the sheet.

3. The sheet of claim 1, wherein said particles of non-dissolvable polymeric materials are of a size ranging from about 0.003 inches to about 0.004 inches.

4. The sheet of claim 1, wherein said particles of non-dissolvable polyolefin polymeric materials are polyethylene or polypropylene.

5. The sheet of claim 1, wherein said sheet has a multiplicity of additional openings therein of a predetermined size and shape and said openings being so constructed as to direct liquids therethrough in one direction and to inhibit the flow of liquids therethrough in the other direction.

6. The sheet of claim 5, wherein said additional openings in said sheet are in the form of tapered capillaries.

7. The sheet of claim 6, wherein said tapered capillaries are in the form of frustums of conical surfaces.

8. The sheet of claim 5, wherein in a given projected open area of the sheet, about five percent or more of the area represents said additional openings.

9. The sheet of claim 5, wherein said additional openings have a mean diameter of about 0.005 inch and are spaced apart an average of about 0.02 inch.

10. An absorptive structure for absorbing and containing fluids from a source exterior of said structure comprising a topsheet, an absorbent element and a back sheet, wherein said topsheet is a liquid permeable material formed essentially from particles of non-dissolvable polyolefin or polyvinylchloride polymeric materials partially fused together by heat and having the fuel and resemblance of soft cloth, said partially fused together particles providing a desired amount of liquid permeability through the spaces provided by the partial fusion of said particles, said particles of a size ranging from about one micron to 2000 microns, said top sheet having a thickness of about 0.0005 inches to about 0.25 inches.

11. The absorptive structure of claim 10, wherein said particles of non-dissolvable polymeric materials are post oriented to improve strength and porosity of said topsheet.

12. The absorptive structure of claim 10, wherein said particles of non-dissolvable polymeric matrials are of a size ranging from bout 0.003 inches to about 0.004 inches.

13. The absorptive structure of claim 10, wherein said particles of non-dissolvable polyolefin polymeric materials are polyethylene or polypropylene.

14. The absorptive structure of claim 10, wherein said topsheet has a multiplicity of additional openings therein of a predetermined size and shape and said openings being so constructed as to direct liquids therethrough in one direction and to inhibit the flow of liquids therethrough in the other direction.

15. The absorptive structure of claim 14, wherein said additional openings in said topsheet are in the form of tapered capillaries.

16. The absorptive structure of claim 15, wherein said tapered capillaries are in the form of frustums of conical surfaces.

17. The absorptive structure of claim 14, wherein in a given projected open area of the porous topsheet, about five percent or more of the area represents said additional openings and said additional openings have a mean diameter of about 0.005 inch and are spaced apart an average of about 0.02 inch.

* * * * *